United States Patent
Rindlav-Westling et al.

(10) Patent No.: US 8,377,498 B2
(45) Date of Patent: Feb. 19, 2013

(54) METHOD FOR PRODUCING A MEDICAL DEVICE WITH A CROSS-LINKED HYDROPHILIC COATING

(75) Inventors: Åsa Rindlav-Westling, Lindome (SE); Sara Richardson, Onsala (SE)

(73) Assignee: Astra Tech AB, Molndal (SE)

( * ) Notice: Subject to any disclaimer, the term of this patent is extended or adjusted under 35 U.S.C. 154(b) by 572 days.

(21) Appl. No.: 12/642,350

(22) Filed: Dec. 18, 2009

(65) Prior Publication Data

US 2010/0159116 A1    Jun. 24, 2010

Related U.S. Application Data

(60) Provisional application No. 61/139,254, filed on Dec. 19, 2008.

(30) Foreign Application Priority Data

Dec. 19, 2008  (EP) ..................................... 08172343

(51) Int. Cl.
*A61L 33/00* (2006.01)
*B05D 3/00* (2006.01)

(52) U.S. Cl. ........................................ 427/2.1; 427/331

(58) Field of Classification Search .................... 427/2.1, 427/331

See application file for complete search history.

(56) References Cited

U.S. PATENT DOCUMENTS 5,094,876 A * 3/1992 Goldberg et al. ............. 428/481
5,100,689 A * 3/1992 Goldberg et al. ............... 600/36
2004/0086722 A1   5/2004 Madsen

FOREIGN PATENT DOCUMENTS

| WO | WO 89/09246 A1 | 10/1989 |
|---|---|---|
| WO | WO 95/29722 A1 | 11/1995 |
| WO | WO 2004/075944 A1 | 9/2004 |
| WO | WO 2006/002644 A2 | 1/2006 |

OTHER PUBLICATIONS

International Search Report issued Aug. 27, 2010, in International Application No. PCT/EP2009/067491.

* cited by examiner

*Primary Examiner* — Timothy Vanoy
(74) *Attorney, Agent, or Firm* — Birch, Stewart, Kolasch & Birch, LLP

(57) ABSTRACT

Disclosed is a production method for medical devices with a hydrophilic coating, which ensures adequate adhesion to the substrate, as well as good water retention and low friction properties. Specifically, the method comprises providing a coating solution comprising a hydrophilic polymer to a surface of a substrate to form a non-cross-linked hydrophilic coating; and irradiating the coated substrate, thereby cross-linking the hydrophilic coating and simultaneously sterilizing the medical device. Hereby, a non-cross linked hydrophilic coating is first obtained which is not fit for use as a catheter coating. However, after the step of irradiating the coated substrate, the hydrophilic coating becomes cross-linked, and fit for use e.g. on a urinary catheter. Further, since one and the same irradiation step is used to effect both cross-linking and sterilization, the production can be made more efficient, using fewer production steps and with a shortened production time.

21 Claims, No Drawings

METHOD FOR PRODUCING A MEDICAL DEVICE WITH A CROSS-LINKED HYDROPHILIC COATING

CROSS REFERENCE TO RELATED APPLICATIONS

This nonprovisional application claims the benefit of U.S. Provisional Application No. 61/139,254 filed on Dec. 19, 2008 under 35 U.S.C. §119(e) and to Patent Application No. 08172343.9 filed in EUROPE on Dec. 19, 2008 under 35 U.S.C. §119(a). The entire contents of all of the above applications is hereby incorporated by reference into the present application.

FIELD OF THE INVENTION

The present invention generally relates to a method for producing a medical device with a hydrophilic surface coating. Specifically, the method is suitable for producing sterile medical devices which present a substrate, such as an elongate shaft, having an outer hydrophilic surface coating, such as a catheter for insertion into a passageway in a human or animal body, and specifically urinary catheters.

BACKGROUND OF THE INVENTION

It is known to coat medical devices, e.g. catheters for introduction into human cavities such as blood vessels, digestive organs and the urinary system, with a hydrophilic coating, at least on the surface of the insertable part which is introduced or comes into contact with mucous membranes, etc., during introduction of the device. An advantage with such a hydrophilic coating is that it becomes extremely slippery when it is swelled with water, preferably immediately before introduction into the human body and thus ensures a substantially painless introduction with a minimum of damage on tissue.

A large number of methods are known for the production of hydrophilic surface coatings. These methods are mainly based on the fact that the substrate to be provided with a hydrophilic surface coating, in the course of one or more process stages with intermediary drying and curing, is coated with one or more layers, which are brought to react with one another in various ways, e.g. by polymerisation initiated by irradiation, by graft polymerisation, by the formation of inter-polymeric network structures, or by direct chemical reaction. A known hydrophilic coating process is e.g. disclosed in EP 0 093 093, where isocyanate is used to form a polyurea network for connecting hydrophilic PVP to the substrate. Further, EP 0 217 771 describes a method of adding an osmolality increasing compound to such a hydrophilic coating in order to improve the water retention properties and low friction of the coating. Further, WO 98/58989 discloses a hydrophilic coating which is cross-linked by means of irradiation, and incorporating a water soluble osmolality increasing compound therein.

The total production process for medical devices with hydrophilic coatings is consequently relatively complex and cumbersome. A suitable substrate should be provided, a hydrophilic coating should be arranged on the substrate, which normally involves a number of timely separated steps, the medical device should be enclosed in a suitable package, and be sterilized, e.g. by means of irradiation or ethylene oxide gas. Due to the large number of steps required for the production, the production takes long time, and is relatively costly.

Accordingly, there is a need for a more time and cost effective production method for medical devices with a hydrophilic coating, while still maintaining adequate adhesion to the substrate, as well as good water retention and low friction properties, and preferably also maintaining biocompatibility to human tissue such as mucous membrane.

SUMMARY OF THE INVENTION

It is a general object of the present invention to alleviate the above-discussed problems. One particular object of the present invention is to provide a more time and cost effective production method for medical devices with a hydrophilic coating, while still providing adequate adhesion to the substrate, as well as good water retention and low friction properties. Other general and specific objects of the invention will in part be obvious and will in part appear hereinafter.

These objects are achieved with the production method according to the appended claims.

According to the invention there is provided a method for producing a medical device with a hydrophilic surface coating, comprising the steps of:
providing a substrate;
applying, in one or more steps, a coating solution comprising a hydrophilic polymer to a surface of said substrate to form a non-cross-linked hydrophilic coating on said substrate;
irradiating the coated substrate, wherein said irradiation is adapted both to cross-link said hydrophilic coating and to simultaneously sterilize the medical device.

The terms "cross-link" and "cross-linking" are here used to denominate a covalently cross-linked connection between polymer chains, where a polymer is defined as a molecule composed of two or more repeating units. The term "coating solution" is here used to denominate a coating medium that can be a true solution or containing non-dissolved or phase separated compounds e.g. dispersion, emulsion, blend, melt, etc.

Notably, even though a non-cross-linked hydrophilic coating is applied on the substrate, this does not preclude provision of other coatings or coating layers on the substrate, which may or may not be cross-linked prior to the irradiation step, and which may or may not be hydrophilic. For example, it is possible to first arrange a cross-linked primer coating on the substrate, and subsequently arrange the non-cross-linked hydrophilic coating on top of said primer layer. However, the non-cross-linked hydrophilic coating is preferably arranged as an outermost layer on the substrate.

By means of the present invention, a non-cross linked hydrophilic coating is first obtained on the substrate, which coating is loosely connected to the substrate, and which is not fit for use as a catheter coating. This coating would immediately be damaged and at least partly fall off if the substrate was subjected to mechanical wear, such as when e.g. introducing it into the urethra of a patient. However, after the step of irradiating the coated substrate, the hydrophilic coating becomes cross-linked, and fit for use e.g. on a urinary catheter.

The coating obtainable by the present invention has excellent properties and enables a very effective production process. Generally, cross-linked coatings have certain advantageous features, such as having a higher abrasion resistance, as compared to the non-cross-linked or physically cross-linked hydrophilic coatings. Apart from a good adherence to the substrate, the coating can also be made to have excellent water retention and low friction properties.

The final product properties are by means of the present invention not obtained until after the irradiation that provide product sterility. Thus, before the final irradiation step, the medical device is not yet ready for its intended use, and is also not sterile.

Further, since one and the same irradiation step is used to effect both cross-linking and sterilization, the production can be made more efficient, using fewer production steps and with a shortened production time.

Still further, the inventive process can be made very environmentally friendly, since few additives, initiators, solvents and the like, are needed.

The inventive concept is based on a hydrophilic, cross-linked polymer coating that is bonded to the substrate by means of irradiation, such as electron beam irradiation. The main idea is that the coating is applied in a simple manner, such as dipping catheter substrates in a single, water-based solution comprising PVP, an osmolality increasing substance and possibly some alcohol-based solvent. The coating can then e.g. be dried onto the catheters, or made to remain as a loosely bonded coating on the substrate in other ways, and preferably enclosed into packages. Finally the device is exposed to irradiation, whereby in this final step i) the coating is cross-linked and simultaneously ii) the product is sterilized.

The radiation dose is preferably selected in order to obtain the desired sterility, and to obtain a sufficient degree of cross-linking. Preferably, the radiation dose is more than 25 kGy, but higher doses, such as more than 100, 150 or even 200 kGy may be required in some situations. The dose required is dependent on inter alia the substrate material chosen, the constituents of the coating solution, the desired slipperiness and abrasion of the coating, etc. Here, the dose represents an aggregated value, which may be provided by a single irradiation shot, or by several consecutive shots. Thus, as an example, a dose of 150 kGy may be obtained by a single shot with 150 kGy, with two shots at 75 kGy, or three shots at 50 kGy. It has surprisingly been found by the present inventors that the same aggregated dose provides essentially the same result in the coating, regardless of if it is provided in a single shot or divided into two or more consecutive shots.

Preferably, the method also comprises the step of enclosing the medical device in a receptacle before the step of irradiation, wherein said receptacle is arranged to maintain the medical device in a sterile condition after irradiation. Hereby, the production process becomes even more simple, since the packaging need not take place in a sterile environment, and the receptacle maintains the sterility of the device after the irradiation.

The receptacle may e.g. be of a plastic material. It is also possible to enclose further components in the receptacle, such as a container or sachet with wetting fluid for subsequent activation of the catheter. It is also possible for the catheter to be arranged directly in contact with a wetting fluid in the container, to continuously be maintained in a activated state.

The irradiation is preferably at least one of electron beam irradiation and gamma irradiation.

The hydrophilic polymer is preferably at least one of: polyvinyl compounds, polylactames, in particular such as polyvinyl pyrrolidones, polysaccharides, heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride. Most preferably, the hydrophilic polymer is polyvinylpyrrolidone.

The substrate is preferably made of a polymer material. The substrate may e.g. comprise at least one of: polyurethanes, latex rubbers, silicon rubbers, other rubbers, polyvinylchloride (PVC), other vinyl polymers, polyesters, polyacrylates, polyamides, biopolymers, polyolefines, thermoplastic elastomers, styrene block copolymers (SEBS, SBS), or polyether block amid (PEBA).

The step of applying the coating solution preferably comprises at least one of dip-coating, spray-coating, powder-coating, injection moulding and extrusion. Dip-coating is presently the preferred method for application of the coating.

The coating solution may further comprise a dissolved osmolality increasing compound, such as sodium chloride. Other osmolality increasing compounds, such as urea and the omsolality increasing compounds discussed in EP 0 217 771 are also feasible, said document hereby incorporated by reference.

The method may further comprise the step of drying the applied coating solution on the substrate, to form a loosely bound coating on said substrate before irradiation. The drying can be made at an elevated temperature, significantly higher than normal room temperature, such as in the range 50-130° C. By means of the drying, it is ensured that the coating remains on its intended place until it is properly bonded to the substrate during the irradiation step.

The coating solution may further comprise a solvent, or a combination of solvents, to improve at least one of the wetting of the substrate and the adhesion between the coating and the substrate. Preferred such solvents for hydrophilic polymers, especially PVP or copolymers thereof, are: water, alcohols such as methanol, ethanol, isopropanol, keto alcohols such as diacetone alcohol, ketones, cyclohexanones, glycols such as ethylene glycol, diethylene glycol, polyethylene glycol, lactones, lactams such as 2-pyrrolidone, N-methyl-pyrrolidone, N-vinylpyrrolidone, amines, ethers, esters, such as ethyl acetate, ethyl lactate, acids such as acetic acid and formic acid, hydrocarbons or chlorinated hydrocarbons. By the use of such solvents, it is ensured that the coating solution is evenly distributed on the substrate surface, and/or that the coating remains in place on the substrate until it is properly bonded to the substrate during the irradiation step.

The coating solution is preferably an aqueous based solution.

All coating constituents can be applied to the substrate in a single step. However, it is also feasible to apply the coating to the substrate in at least two separate steps.

In a preferred embodiment, the step of applying the coating solution to the surface of the substrate comprises the substeps of: applying a primer coating to the substrate; curing the primer coating; and applying a coating solution comprising a hydrophilic polymer to the substrate. The step of curing can e.g. comprise at least one of drying, curing at an elevated temperature and curing by UV-irradiation. Hereby, the primer coating is secured to the substrate surface before the arrangement of the second coating solution, which provides a better adhesion of the second coating solution to the substrate until it is properly cross-linked during the irradiation step.

The method may also comprise the additional step of pretreatment of the surface of the substrate prior to applying the coating solution, wherein the pretreatment provides at least one of an increase in wettability of the surface and introduction of functional groups. This is particularly advantageous when aqueous coating solutions are used. For example, the pretreatment may comprise at least one of a plasma and a corona modification. The oxygen plasma and corona treatment introduces oxygen containing groups in the surface, which makes the surface more hydrophilic. Specifically, plasma treatment with oxygen creates covalently bonded oxygen containing groups in the surface, such as —OH, —C=O, or C=O—OH. Plasma treatment can also be made using other substances than oxygen, for instance nitrogen, air, ammonia, acrylic acid, fluorine or silica containing compounds, thereby introducing various functional groups on the substrate surface. The plasma treatment may also effect a cleansing of the surface and a certain degree of etching. The effect of the plasma treatment can be controlled by the plasma treatment parameters in accordance with the specific substrate material at hand. The plasma treatment can be performed either in vacuum or in atmospheric environment. The corona treatment is preferably performed in atmospheric environment, and introduces oxygen groups in the surface by means of the oxygen in the ambient air.

It is also possible to provide a thickener that increases the viscosity at lower shear rates in the coating solution, in order to obtain a better adherence of the coating solution to the substrate before irradiation. A thickener in the coating solution makes it possible to avoid drop rolling in the coating process. In e.g. a dip-coating process the withdrawal of the catheters from the coating solution leads to formation of drops that tend to roll over the catheter and finally stay at the lower edge of the catheter. This results in an uneven coating of the catheter. By adding a thickener that increases the viscosity at lower shear rates in the coating solution, the drop rolling could be stopped or reduced, leading to a more smooth coating of the catheter.

The coating solution may further comprise constituents that are made reactive under the influence of radiation and contribute to increased cross-linking during irradiation. Such constituents may e.g. be initiators, monomers, such as radically polymerisable vinyl monomers, oligomers, prepolymers or components containing vinylic groups. For example, the constituents may be a prepolymer containing reactive sites cross-linkable through reaction of vinylic unsaturated groups and optionally one or more saturated polymers. It is also feasible to introduce an initiator that produces radicals under the influence of LTV, e-beam or γ-irradiation. The radicals can create covalent bonds between molecules, in this particular case between prepolymer molecules, hydrophilic polymer molecules, other added molecules in the coating solution and/or molecules in the surface of the catheter raw material. By the use of such constituents contributing to increase cross-linking during irradiation, it becomes possible to use a lower radiation dose to get sufficient cross-linking of the coating and bonding of the coating to the substrate surface.

The production method according to the present invention is particularly suitable for the production of catheters, and specifically urinary catheters. However, the production method is also useful for many other types of medical devices having a hydrophilic coating. Accordingly, the method according to the present invention is not limited to urinary catheters. Examples of such other medical devices for which the present invention is useful are vascular catheters and other types of catheters, endo and laryngoscopes, tubes for feeding, or drainage or endotracheal use, condoms, wound dressings, contact lenses, implants, extracorporeal blood conduits, membranes e.g. for dialysis, blood filters and devices for circulatory assistance.

These and other aspects of the inventive concept will be apparent from and elicited with reference to the embodiments described hereinafter.

DESCRIPTION OF PREFERRED EMBODIMENTS AND EXPERIMENTAL RESULTS

In the following detailed description preferred embodiments of the invention will be described. However, it is to be understood that features of the different embodiments are exchangeable between the embodiments and may be combined in different ways, unless anything else is specifically indicated. The hydrophilic catheters may be used for many different purposes, and for insertion into various types of body-cavities. However, the following discussion is in particular concerned with the preferred field of use, urinary catheters, even though the invention is not limited to this particular type of catheters. However, it is to be appreciated by those skilled in the art that the inventive concept is not limited to this type of devices, but could also be used in many other types of medical devices that are to be sterilised with radiation.

At least a part of the elongate tube forms an insertable length to be inserted through a body opening of the user, such as the urethra in case of a urinary catheter. By insertable length is normally, in the context of a hydrophilic catheter, meant that length of the elongate tube which is coated with a hydrophilic material, for example PVP, and which is insertable into the urethra of the patient. Typically, this will be 80-140 mm for a female patient and 200-350 mm for a male patient.

The elongate shaft/tube of the catheter is made of a substrate material. The substrate may be made from any polymer material, which are well-known in the technical field and to which the said hydrophilic polymers can be made to adhere, such as polyurethanes, latex rubbers, silicon rubbers, other rubbers, polyvinylchloride (PVC), other vinyl polymers, polyesters, polyacrylates, polyamides, biopolymers, polyolefines, thermoplastic elastomers, styrene block copolymers (SEBS, SBS), or polyether block amid (PEBA), or combinations of the above-mention polymers.

The hydrophilic coating is arranged on at least part of the substrate forming the catheter shaft. The hydrophilic polymer coating may comprise material selected from polyvinyl compounds, polylactames, in particular such as polyvinyl pyrrolidones, polysaccharides, heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride, or combinations of the above-mention polymers The preferred hydrophilic polymer is polyvinylpyrrolidone.

The coating may also comprise an osmolality-increasing compound, as is e.g. taught in EP 0 217 771.

Some preferred examples of methods for applying a hydrophilic surface coating to the substrate will now be discussed in greater detail.

In the experimental tests to be discussed in the following, substrates made of the following substrate materials were used:
Polyether block amid (PEBA)
Polyvinyl chloride (PVC)
Styrene block copolymers (SBS)
SEBS-based thermoplastic elastomer Meliflex
SEBS-based thermoplastic elastomer Mediprene The coatings prepared in accordance with the present invention will be discussed in more detail in the following.

As a comparative example, substrates were coated in accordance with a known coating process in which isocyanate is used to form a polyurea network for binding PVP. More specifically, the coating according to the comparative example was prepared by dipping the substrates in a primer solution comprising a diisocyanate (named Desmodur IL), which is dissolved in methylene chloride to a concentration of 2% (weight/volume), for 15 seconds. The catheters were thereafter dried at ambient temperature for 60 seconds, and were then dipped for 3 seconds in a solution containing 6% (weight/volume) of polyvinylpyrrolidone (PVP K90) dissolved in methylene chloride. The catheters were then allowed to flush off at 35° C. for 30 minutes, and then cured for 60 minutes at 80° C., and were finally allowed to cool to room temperature and rinsed in water. The concentrations of the coating solution components in the following examples are given in weight %.

The analysis of the coated catheters involves measurement of water retention, both immediately after wetting and after leaching, and friction measurements, both by measuring the friction in accordance with the standard ASTM D 1894 and manually by having test persons determining the friction by hand.

The water retention of the catheters was determined by wetting the catheters in water during 30 sec., and determining the water content (mg/cm$^2$) in the hydrophilic coating after 1 and/or 6 minutes drying in air. The water content was determined by weighing the catheters before wetting, to obtain a reference weight, and to weigh the catheters a certain time after wetting, and subtracting the reference weight from this measurement. The area of coating is measured. The obtained weight/cm$^2$ difference is a measure on the water content being held by the hydrophilic coating at the time of measurement.

Water retention after leaching was determined in the same way, but with the initial step of wetting the catheters for a prolonged period of time (30 minutes) in 35° C. tempered water and drying for 24 hours. The water retention after leaching provides an estimation of the adhesion of the hydrophilic coating to the substrate.

Experiment 1

One-Step Dipping with Solvent

In a first experiment, catheter substrates were coated in a coating solution comprising 6.7% PVP K90 in a solvent. The solvent comprised 75% isobutanol and 25% ethyl acetate. The catheters were dried and then enclosed in receptacles, and electron beam irradiated at a process-dose of 100 kGy or 200 kGy.

As a comparison, the same catheter substrates were coated according to the comparative example discussed above. These catheters were packed in the same type of receptacles, and sterilized by being electron beam irradiated at 56 kGy.

The water retention of the catheters was measured, before and after leaching, and the results are presented in the following Table 1.

TABLE 1

Water retention [mg/cm$^2$] in coating before and after leaching

| Example | Material | Radiation dose [kGy] | Water retention after 1 minute [mg/cm$^2$] | Water retention after leaching after 1 minute [mg/cm$^2$] |
|---|---|---|---|---|
| Inv. Ex. | PEBA | 100 | 13 | 3 |
| Inv. Ex. | PEBA | 200 | 12 | 7 |
| Comp. Ex. | PEBA | 56 | 12 | 8 |
| Inv. Ex. | PVC | 100 | 10 | 8 |
| Inv. Ex. | PVC | 200 | 11 | 6 |
| Comp. Ex. | PVC | 56 | 8 | 4 |
| Inv. Ex. | Meliflex | 100 | 11 | 2 |
| Inv. Ex. | Meliflex | 200 | 10 | 4 |
| Comp. Ex. | Meliflex | 56 | 8 | 6 |
| Inv. Ex. | SBS | 100 | 12 | 1 |
| Inv. Ex. | SBS | 200 | 12 | 5 |

Thus, all the catheters prepared in accordance with the invention were found to have a water retention after 1 minute which was similar to or even better than the comparative examples. Further, the water retention after leaching was acceptable for all the catheters prepared in accordance with the invention when irradiated by 200 kGy. For the PVC substrates the water retention after leaching was even improved compared to the comparative examples, both when irradiated by 100 kGy and 200 kGy.

Experiment 2

One-Step Dipping with Different Solvent and Varied Radiation Dose

In a second experiment, catheter substrates made of PEBA were coated in a coating solution comprising 7% PVP K90 in a solvent of methylene chloride. The catheters were dried and then enclosed in receptacles, and irradiated by electron beam radiation at various doses. The total aggregated doses were divided among 1-4 shots.

As a comparison, the same catheter substrates were coated according to the comparative example discussed above. These catheters were packed in the same type of receptacles, and sterilized by electron beam irradiation at a process-dose of 56 kGy.

The water retention of the catheters was measured, before and after leaching, and the results are presented in the following Table 2.

TABLE 2

Water retention [mg/cm$^2$] in coating before and after leaching

| Example | Material | Radiation dose [kGy] | Water retention after 1 minute [mg/cm$^2$] | Water retention after leaching after 1 minute [mg/cm$^2$] |
|---|---|---|---|---|
| Inv. Ex. | PEBA | 200 | 14 | 10 |
| Inv. Ex. | PEBA | 3 × 100 | 14 | 10 |
| Inv. Ex. | PEBA | 2 × 100 | 16 | 10 |
| Inv. Ex. | PEBA | 2 × 56 | 16 | 11 |
| Inv. Ex. | PEBA | 3 × 56 | 15 | 10 |
| Inv. Ex. | PEBA | 4 × 56 | 14 | 12 |
| Comp. Ex. | PEBA | 56 | 12 | 8 |

Thus, all the catheters prepared in accordance with the invention were found to have a water retention after 1 minute which was better than the comparative example. Further, the water retention after leaching was better for all the catheters prepared in accordance with the invention than the comparative example. Further, there is no significant difference between the inventive examples where the total radiation dose is divided among two or more shots, compared to when the total dose is provided in one single shot.

The coefficient of friction was also determined for some of the examples, and was 0.06μ for the inventive example irradiated by 2×56 kGy, 0.03μ for the inventive example irradiated by 3×56 kGy, 0.02μ for the inventive example irradiated by 4×56 kGy and 0.04μ for the comparative example. Thus, the friction is acceptable for all the examples.

Experiment 3

Two-Step Dipping

In a third experiment, catheter substrates made of PEBA, PVC and Meliflex were coated in a two-step dipping process. The first coating solution comprised 4% PVP K90 in a solvent of methylene chloride. The second coating solution comprised 4% PVP K90 and 15% NaCl in water. The catheters were dried both after the first and second dipping steps, and then enclosed in receptacles, and electron beam irradiated at 2×56 kGy or 3×56 kGy.

As a comparison, the same catheter substrates were coated according to the comparative example discussed above. NaCl was then provided to the catheters in accordance with the process disclosed in EP 0 217 771. These catheters were packed in the same type of receptacles, and sterilized by electron beam irradiation at 56 kGy.

The friction was determined manually, and was found to be acceptable for all the examples. Further, the water retention after leaching after 1 minute for the inventive examples were found to be similar to or even improved compared to the comparative example.

Experiment 4

Pretreatment of Substrate Surface

In a fourth experiment, catheter substrates made of Meliflex, Mediprene and SBS were used. Before coating, the substrates were plasma treated with oxygen by use of 300 W HF power, and 0.7 mbar gas flow pressure for 5 minutes. After the plasma treatment, the catheters were dipped in one of the following coating solutions:

Coating A) A first coating solution comprising 5% PVP K90 in a solvent of methylene chloride, and a second coating solution comprising 17% NaCl and 13% PVP K30 in water. (Two-dip process)

Coating B) A first coating solution comprising 5.5% PVP K90 in a solvent of ethanol, and a second coating solution comprising 17% NaCl and 13% PVP K30 in water. (Two-dip process)

Coating C) A coating solution comprising 6.5% PVP K90 and 10% NaCl in water. (One-Dip Process)

The catheters were dried after dipping, and in case of the two-dip process both after the first and second dipping steps, in an oven at 80° C. Subsequently, the catheters were enclosed in receptacles, and electron beam irradiated at process-doses of 2×100 kGy.

The catheters were analyzed in respect of slipperiness, water retention before and after leaching, and friction. The results are presented in the following Tables 3-5. The measurement of friction was made in accordance with the above-discussed standard ASTM.D 1894, and both average friction and coefficient of friction (COF) were determined.

TABLE 3

Water retention [mg/cm$^2$] in coating before leaching

| Example | Material | Coating | Water retention after 1 minute [mg/cm$^2$] | Water retention after 6 minutes [mg/cm$^2$] |
|---|---|---|---|---|
| Inv. Ex. | Meliflex | A | 10 | 8 |
| Inv. Ex. | Meliflex | B | 8 | 5 |
| Inv. Ex. | Meliflex | C | 11 | 8 |
| Inv. Ex. | Mediprene | A | 11 | 7 |
| Inv. Ex. | Mediprene | B | 10 | 6 |
| Inv. Ex. | Mediprene | C | 12 | 9 |
| Inv. Ex. | SBS | A | 12 | 9 |
| Inv. Ex. | SBS | B | 8 | 5 |

TABLE 4

Water retention [mg/cm$^2$] in coating after leaching

| Example | Material | Coating | Water retention after leaching after 1 minute [mg/cm$^2$] | Water retention after leaching after 6 minutes [mg/cm$^2$] |
|---|---|---|---|---|
| Inv. Ex. | Meliflex | A | 7 | 6 |
| Inv. Ex. | Meliflex | B | 5 | 3 |
| Inv. Ex. | Meliflex | C | 6 | 5 |
| Inv. Ex. | Mediprene | A | 10 | 9 |
| Inv. Ex. | Mediprene | B | 5 | 3 |
| Inv. Ex. | Mediprene | C | 5 | 4 |
| Inv. Ex. | SBS | A | 11 | 10 |
| Inv. Ex. | SBS | B | 4 | 2 |

TABLE 5

Average friction and COF

| Example | Material | Coating | Average friction [N] | COF [μ] |
|---|---|---|---|---|
| Inv. Ex. | Meliflex | A | 0.09 | 0.05 |
| Inv. Ex. | Meliflex | B | 0.07 | 0.03 |
| Inv. Ex. | Meliflex | C | 0.06 | 0.03 |
| Inv. Ex. | Mediprene | A | 0.12 | 0.06 |
| Inv. Ex. | Mediprene | B | 0.10 | 0.05 |
| Inv. Ex. | Mediprene | C | 0.07 | 0.04 |
| Inv. Ex. | SBS | A | 0.11 | 0.06 |
| Inv. Ex. | SBS | B | 0.17 | 0.09 |

The result of these measurements show that all catheters, independent of substrate material and coating solution, exhibit water retention values that fulfill the requirements for commercial hydrophilic urinary catheters. Further, even though the water retention after leaching varied significantly, all catheters fulfilled the requirements for water retention after leaching, indicating that the coating adhered sufficiently to the substrate surface in all the examples. Further, all the catheters obtained COF values and average friction values that are required for hydrophilic urinary catheters.

Experiment 5

Two-Step Process with Primer Coating

In a fifth experiment, catheter substrates made of Mediprene were coated in a two-step process. In a first step, a primer coating was applied to the substrate by means of dipping. The primer coating solution containers 96.9% of ethanol, 2% of PVP K90, 0.1% of benzophenone and 1% of urethane acrylate oligomer. The primer coating solution was then cured by means of UV-irradiation at 254 nm. Subsequently, a second coating solution comprising 7% PVP K90 in ethanol was applied to the substrate by dipping. The catheters were then dried, enclosed in receptacles, and electron beam irradiated at process doses of 100 kGy or 2×100 kGy.

Further, catheters were also prepared without the primer coating solution and UV-curing, as well as with the primer coating solution but without UV-curing. For comparison, catheters were also prepared using only the primer coating solution and the UV-curing, but without the second coating solution and without e-beam irradiation, or with the second coating solution but without e-beam irradiation.

The friction and durability of the final coating of the above-discussed catheters were evaluated after 10 cycles using a Harland FTS Friction Tester, available from Harland Medical Systems, with a clamp force of 100 g and a pull speed of 1.0 cm/s.

TABLE 6

| | | | | | Friction |
|---|---|---|---|---|---|
| Experiment | Primer coating solution | UV-curing | Second coating solution | E-beam radiation dose | Friction (g) |
| 1 | X | X | — | — | 94 |
| 2 | X | X | X | — | 71 |
| 3 | X | X | X | 200 kGy | 1.3 |
| 4 | — | — | X | 200 kGy | 12 |
| 5 | X | — | X | 200 kGy | 1.1 |
| 6 | X | X | X | 100 kGy | 1.2 |

The results of these measurements clearly show that:
The relatively high friction for Exp. 1 and 2 is primarily due to low adherence to the substrate, which results in wearing off of the coating during the repeated friction testing.
Use of the second solution without e-beam irradiation provides a small improvement in friction (Exp. 2 better than Exp. 1), but a very significant improvement is obtained when the coating is also subjected to e-beam irradiation (Exp. 3 significantly better than Exp. 1 and 2).
The primer coating solution, containing reactive constituents, significantly improves the friction (Exp. 3 and 5 significantly better than Exp. 4).
In addition, complementary experiment showed that reactive constituents in the primer coating solution, enables use of much lower e-beam radiation dose and still obtain a similar friction (Exp. 6 and 3 about equally good).

CONCLUSION AND SUMMARY

The invention has now been discussed in relation to different embodiments. However, it should be appreciated by those versed in the art that several further alternatives are possible. For example, many other substrate materials, hydrophilic polymers and solvents may be used. It is further possible to use the invention for other types of catheters than urinary catheters, such as vascular catheters or the like, or for other types of medical devices having a hydrophilic coating.

It will be appreciated by those versed in the art that several such alternatives similar to those described above could be used without departing from the spirit of the invention, and all such modifications should be regarded as a part of the present invention, as defined in the appended claims.

The invention claimed is:
1. A method for producing a medical device with a hydrophilic surface coating, comprising the steps of:
providing a substrate;
applying, in one or more steps, a coating solution comprising a hydrophilic polymer to a surface of said substrate to form a non-cross-linked hydrophilic coating on said substrate;
enclosing the medical device in a receptacle; and
irradiating the coated substrate, wherein said irradiation is adapted both to cross-link said hydrophilic coating and to simultaneously sterilize the medical device;
wherein said step of enclosing the medical device in a receptacle is made before the step of irradiation, and wherein said receptacle is arranged to maintain the medical device in a sterile condition after irradiation.
2. The method of claim 1, wherein the irradiation is at least one of electron beam irradiation and gamma irradiation.
3. The method of claim 2, wherein the hydrophilic polymer is at least one of: polyvinyl compounds, polylactames polysaccharides, polyurethanes, polyacrylates, polyhydroxy-acrylates, polymethacrylates, polyacrylamides, polyalkylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic anhydride.
4. The method of claim 1, wherein the hydrophilic polymer is at least one of: polyvinyl compounds, polylactames, polysaccharides, polyurethanes, polyacrylates, polyhydroxy-acrylates, polymethacrylates, polyacrylamides, polyalkylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anhydride.
5. The method of claim 4, wherein the hydrophilic polymer is at least one of: polyvinyl compounds, polylactames, polysaccharides, polyurethanes, polyacrylates, polyhydroxy-acrylates, polymethacrylates, polyacrylamides, polyalkylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anhydride.
6. The method of claim 1, wherein the substrate is made of a polymer material.
7. The method of claim 1, wherein the substrate comprises at least one of: polyurethanes, latex rubbers, silicon rubbers, other rubbers, polyvinylchloride (PVC), other vinyl polymers, polyesters, polyacrylates, polyamides, biopolymers, polyolefines, thermoplastic elastomers, styrene block copolymers (SEBS, SBS), or polyether block amid (PEBA).
8. The method of claim 1, wherein the coating solution further comprises a dissolved osmolality increasing compound.
9. The method of claim 1, wherein the coating solution further comprises a solvent to improve at least one of the wetting of and the adhesion between the coating and the substrate.
10. The method of claim 1, wherein the coating solution is an aqueous or alcohol based solution.
11. The method of claim 1, wherein all coating constituents are applied to the substrate in a single step.
12. The method of claim 1, wherein the coating is applied to the substrate in at least two separate steps.
13. The method of claim 12, wherein the step of applying a coating solution to the surface of the substrate comprises the sub-steps of:

applying a primer coating to the substrate;
drying or curing said primer coating; and
applying a coating solution comprising a hydrophilic polymer to the substrate.

14. The method of claim 13, wherein said step of curing comprises at least one of drying, or curing at an elevated temperature and curing by UV-irradiation.

15. The method of claim 1, further comprising the step of pretreatment of the surface of the substrate prior to applying the coating solution, said pretreatment providing at least one of an increase in wettability of the surface and introduction of functional groups.

16. The method of claim 15, wherein said pretreatment comprises at least one of a plasma and a corona modification.

17. The method of claim 1, wherein said coating solution further comprises constituents that are made reactive under the influence of radiation and contribute to increased cross-linking during irradiation.

18. The method of claim 1, wherein the irradiation provides a total radiation dose of more than 25 kGy.

19. The method of claim 1, wherein the irradiation provides a total radiation dose of more than 100 kGy.

20. The method of claim 1, wherein the irradiation provides a total radiation dose of more than 150 kGy.

21. The method of claim 1, wherein the irradiation provides a total radiation dose of more than 200 kGy.

* * * * *